US00PP21043P2

(12) United States Plant Patent
Kerley et al.

(10) Patent No.: US PP21,043 P2
(45) Date of Patent: Jun. 1, 2010

(54) ***PETUNIA* PLANT NAMED 'KERMINIBLUE'**

(50) Latin Name: *Petunia×hybrida*
Varietal Denomination: Kerminiblue

(76) Inventors: David William Kerley, Bethany, 49 Station Road, Over, Cambridge CB24 5NJ (GB); Priscilla Grace Kerley, Bethany, 49 Station Road, Over, Cambridge CB24 5NJ (GB)

( * ) Notice: Subject to any disclaimer, the term of this patent is extended or adjusted under 35 U.S.C. 154(b) by 0 days.

(21) Appl. No.: 12/229,600

(22) Filed: Aug. 25, 2008

(51) Int. Cl.
*A01H 5/00* (2006.01)

(52) U.S. Cl. ..... Plt./357

(58) Field of Classification Search ..... Plt./356
See application file for complete search history.

(56) References Cited

U.S. PATENT DOCUMENTS

PP15,480 P2 * 1/2005 Hanes ..... Plt./356

OTHER PUBLICATIONS

Canadian Food Inspection Agency; cultivar cited 'Kerminiblue'.*

* cited by examiner

*Primary Examiner*—Susan B McCormick Ewoldt
(74) *Attorney, Agent, or Firm*—C. A. Whealy

(57) ABSTRACT

A new and distinct cultivar of *Petunia* plant named 'Kerminiblue', characterized by its outwardly spreading to trailing growth habit; freely branching habit; early and freely flowering habit; dark violet blue-colored flowers; and good garden performance.

2 Drawing Sheets

Botanical designation: *Petunia×hybrida.*
Cultivar denomination: 'Kerminiblue'.

BACKGROUND OF THE INVENTION

The present invention relates to a new and distinct cultivar of *Petunia,* botanically known as *Petunia×hybrida* and hereinafter referred to by the name 'Kerminiblue'.

The new *Petunia* plant is a product of a planned breeding program conducted by the Inventors in Over, Cambridge, United Kingdom. The objective of the breeding program is to create new trailing *Petunia* cultivars with dark violet blue-colored flowers.

The new *Petunia* plant originated from a cross-pollination made by the Inventors in August, 2005 in Over, Cambridge, United Kingdom of a proprietary selection of *Petunia×hybrida* identified as code number 05-227-1, not patented, as the female, or seed, parent with a proprietary selection of *Petunia×hybrida* identified as code number 05-227-3, not patented, as the male, or pollen, parent. The new *Petunia* was discovered and selected by the Inventors as a single flowering plant within the progeny of the stated cross-pollination in a controlled greenhouse environment in Over, Cambridge, United Kingdom in May, 2006.

Asexual reproduction of the new *Petunia* plant by terminal cuttings in a controlled greenhouse environment in Over, Cambridge, United Kingdom since September, 2006, has shown that the unique features of this new *Petunia* plant are stable and reproduced true to type in successive generations.

SUMMARY OF THE INVENTION

Plants of the new *Petunia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Kerminiblue'. These characteristics in combination distinguish 'Kerminiblue' as a new and distinct cultivar of *Petunia:*

1. Outwardly spreading to trailing growth habit.
2. Freely branching habit.
3. Early and freely flowering habit.
4. Dark violet blue-colored flowers.
5. Good garden performance.

Plants of the new *Petunia* can be compared to plants of the female parent selection. Plants of the new *Petunia* differ from plants of the female parent selection in the following characteristics:

1. Plants of the new *Petunia* are more trailing than and not as upright as plants of the female parent selection.
2. Plants of the new *Petunia* are larger than plants of the female parent selection.
3. Plants of the new *Petunia* have smaller flowers than plants of the female parent selection.
4. Plants of the new *Petunia* and the female parent selection differ in flower color as plants of the female parent selection have blue-colored flowers.

Plants of the new *Petunia* can be compared to plants of the male parent selection. Plants of the new *Petunia* differ from plants of the male parent selection in the following characteristics:

1. Plants of the new *Petunia* have smaller flowers than plants of the male parent selection.
2. Plants of the new *Petunia* have single flowers whereas plants of the male parent selection have semi-double flowers.

Plants of the new *Petunia* can also be compared to plants of the *Petunia* 'Conviolet', disclosed in U.S. Plant Pat. No. 13,510. In side-by-side comparisons conducted in Over, Cambridge, United Kingdom, plants of the new *Petunia* differed from plants of 'Conviolet' in the following characteristics:

1. Plants of the new *Petunia* were more freely branching than plants of 'Conviolet'.
2. Plants of the new *Petunia* had shorter leaves and leaf petioles than plants of 'Conviolet'.
3. Plants of the new *Petunia* were more freely flowering than plants of 'Conviolet'.
4. Plants of the new *Petunia* and 'Conviolet' differed in flower color as plants of 'Conviolet' had lighter violet-colored flowers.

BRIEF DESCRIPTION OF THE PHOTOGRAPHS

The accompanying colored photographs illustrate the overall appearance of the new *Petunia* plant, showing the colors as true as it is reasonably possible to obtain in colored reproductions of this type. Colors in the photographs may differ slightly from the color values cited in the detailed botanical description which accurately describe the colors of the new *Petunia* plant.

The photograph on the first sheet comprises a side perspective view of typical plants of 'Kerminiblue' grown in a hanging basket container.

The photograph on the second sheet is a close-up view of typical flowers of 'Conviolet' (top) and 'Kerminiblue' (bottom).

DETAILED BOTANICAL DESCRIPTION

The aforementioned photographs and following observations, measurements and values describe plants grown in Over, Cambridge, United Kingdom, under commercial practice during the summer in a glass-covered greenhouse with day temperatures ranging from 18° C. to 28° C., night temperatures ranging from 14° C. to 20° C. and light levels averaging 50 kilolux. Rooted young plants had been growing for four months when the photographs and description were taken. Plants were pinched one time before planting. In the following description, color references are made to The Royal Horticultural Society Colour Chart, 1995 Edition, except where general terms of ordinary dictionary significance are used.

Botanical classification: *Petunia×hybrida* 'Kerminiblue'.

Parentage:

*Female, or seed, parent.*—Proprietary selection of *Petunia×hybrida* identified as code No. 05-227-1, not patented.

*Male, or pollen, parent.*—Proprietary selection of *Petunia×hybrida* identified as code No. 05-227-3, not patented.

Propagation:

*Type.*—By terminal cuttings.

*Time to initiate roots, summer.*—About ten days at temperatures of 21° C.

*Time to initiate roots, winter.*—About two weeks at temperatures of 21° C.

*Time to produce a rooted young plant, summer.*—About 30 days at temperatures of 20° C.

*Time to produce a rooted young plant, winter.*—About 45 days at temperatures of 20° C.

*Root description.*—Fine, fibrous; white in color.

*Rooting habit.*—Moderately free branching; moderately dense.

Plant description:

*Plant and growth habit.*—Outwardly spreading to trailing growth habit. Freely branching habit with about 16 lateral branches developing per plant. Moderately vigorous growth habit.

*Plant height.*—About 39 cm.

*Plant diameter.*—About 73 cm.

Lateral branch description:

*Length.*—About 44 cm.

*Diameter.*—About 3 mm.

*Internode length.*—About 2.9 cm.

*Aspect.*—Initially outwardly spreading to trailing.

*Texture.*—Slightly pubescent.

*Color.*—Close to 144B.

Foliage description:

*Arrangement.*—Before flowering, alternate, simple; after flowering, opposite, simple.

*Length.*—About 4.4 cm.

*Width.*—About 2.9 cm.

*Shape.*—Elliptic.

*Apex.*—Acute.

*Base.*—Acute.

*Margin.*—Entire.

*Texture, upper surface.*—Smooth, glabrous.

*Texture, lower surface.*—Slightly pubescent.

*Venation pattern.*—Pinnate; arcuate.

*Color.*—Developing leaves, upper surface: Close to 137B. Developing leaves, lower surface: Close to 146A. Fully expanded leaves, upper surface: Close to 137A; venation, close to 144C. Fully expanded leaves, lower surface: Close to 146B; venation, close to 144B.

*Petiole length.*—About 2 mm.

*Petiole diameter.*—About 1.8 mm.

*Petiole texture, upper and lower surfaces.*—Slightly pubescent.

*Petiole color, upper and lower surfaces.*—Close to 144A.

Flower description:

*Flower arrangement and habit.*—Single-type salver-form flowers; singly arising from leaf axils. Freely flowering habit with usually about 69 flowers developing per plant. Flowers face mostly outwardly.

*Fragrance.*—Slightly fragrant, pleasant.

*Natural flowering season.*—Plants flower continuously during the summer in the United Kingdom.

*Flower longevity.*—Individual flowers last about five days on the plant; flowers persistent.

*Flower diameter.*—About 6.5 cm.

*Flower throat diameter.*—About 1 cm.

*Flower tube length.*—About 3 cm.

*Flower tube diameter (base).*—About 3 mm.

*Flower bud.*—Shape: Ovoid. Length: About 4.4 cm. Diameter: About 7 mm. Color: Close to 90A.

*Corolla.*—Arrangement: Five petals fused at the base and opening into a flared trumpet. Petal length from throat: About 3 cm. Petal lobe width: About 3 cm. Petal shape: Spatulate. Petal apex: Cuspidate. Petal margin: Entire. Petal texture, upper and lower surfaces: Smooth, glabrous. Throat texture: Smooth, glabrous. Tube texture: Pubescent. Color: Petals, when opening and fully opened, upper surface: Close to more purple than 89A; color becoming closer to 89A with development; venation, close to 202A becoming closer to 79A at the margins. Petals, when opening and fully opened, lower surface: Close to 87A; venation, close to 79A. Flower throat: Darker than 89A; venation, darker than 79A. Flower tube: Close to 79A; venation, close to 144B occasionally overlain with close to 79A.

*Calyx.*—Arrangement: One star-shaped calyx tube with five sepals fused at the base per flower. Sepal length: About 1.6 cm. Sepal width: About 5 mm. Sepal shape: Narrowly oblong. Sepal apex: Obtuse. Sepal margin: Entire. Sepal texture, upper and lower surfaces: Pubescent. Color, immature and mature, upper surface: Close to 141A. Color, immature and mature, lower surface: Close to 143A.

*Peduncles.*—Length: About 4 cm. Diameter: About 1.5 mm. Angle: About 45° from the stem axis. Strength: Strong. Texture: Pubescent. Color: Close to 143B; distally, overlain with close to 177B.

*Reproductive organs.*—Stamens: Quantity: Five per flower. Anther shape: Oblong. Anther length: About 2 mm. Anther color: Close to 84D. Pollen amount: Abundant. Pollen color: Close to 198D. Pistils: Quantity: One per flower. Pistil length: About 1.7 cm. Style length: About 1.5 cm. Style color: Close to 145C; distally, overlain with close to 86A. Stigma shape: Oval. Stigma color: Close to 144B. Ovary color: Close to 145A. Seed/fruit: Seed and fruit development have not been observed on plants of the new *Petunia*.

Garden performance: Plants of the new *Petunia* have been observed to have good garden performance and tolerate wind, rain and temperatures ranging from about 4° C. to about 40° C.

Pathogen/pest resistance: Plants of the new *Petunia* have not been observed to be resistant to pathogens and pests common to *Petunia*.

It is claimed:

1. A new and distinct *Petunia* plant named 'Kerminiblue' as illustrated and described.

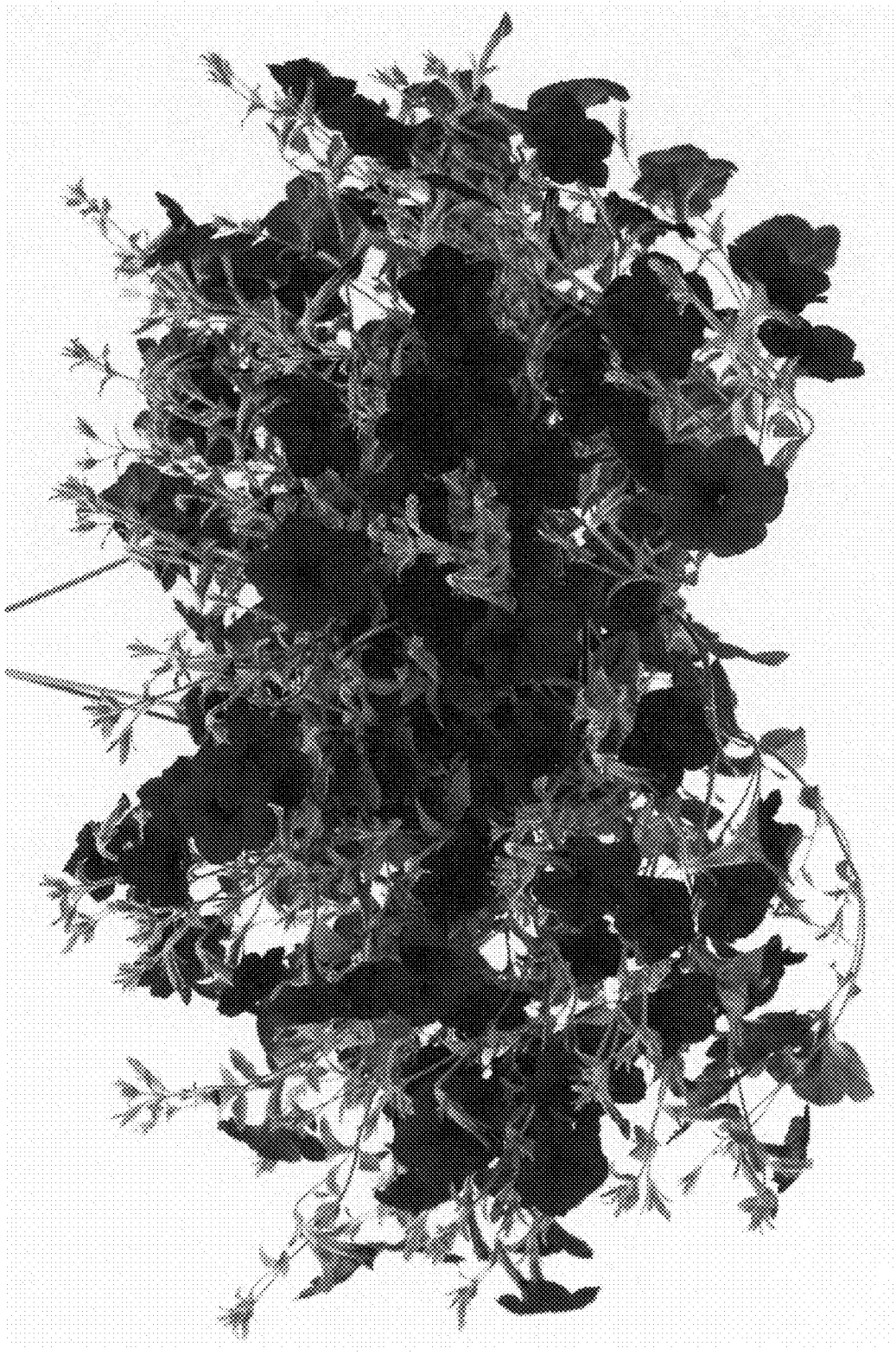

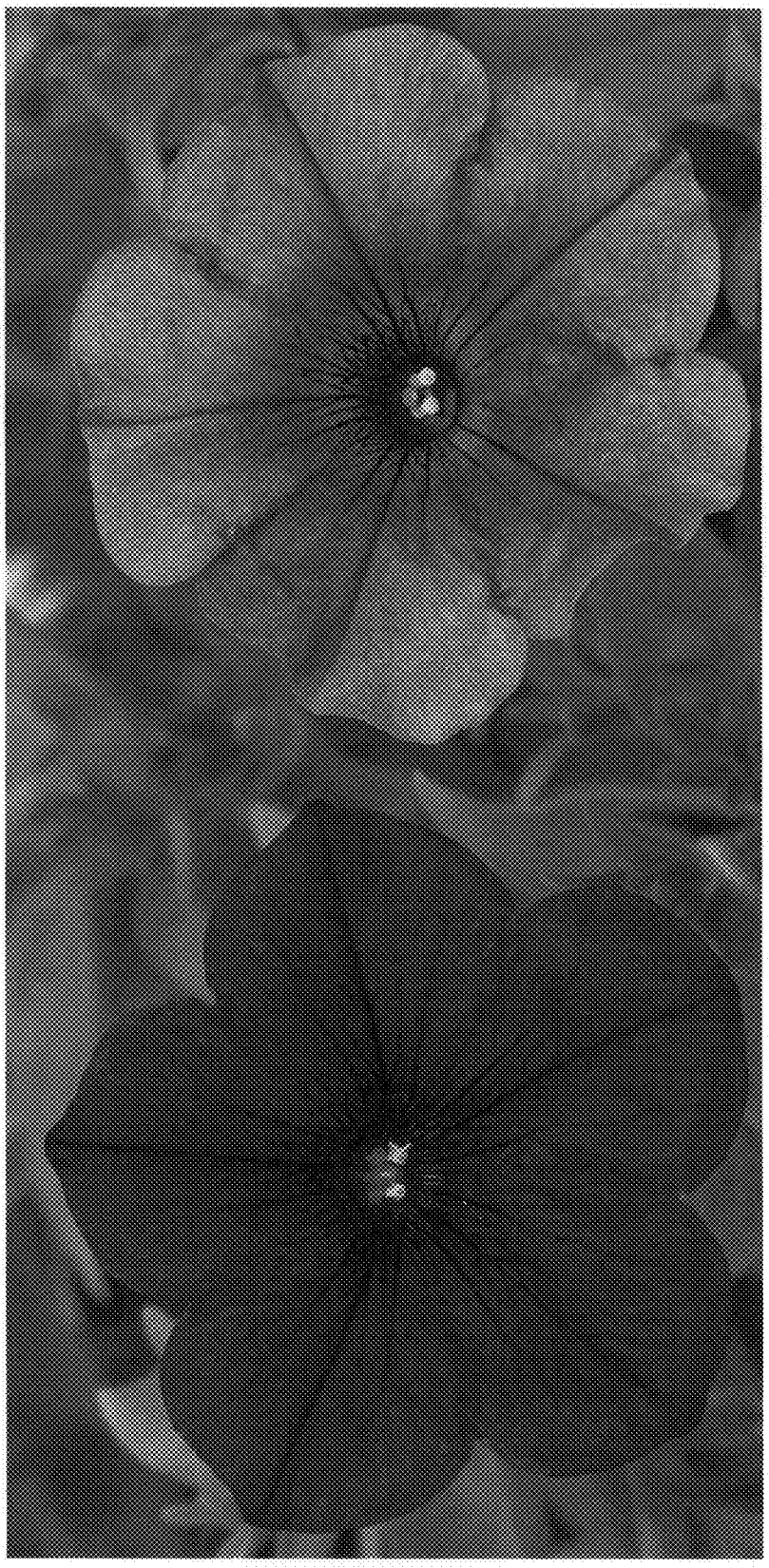

* * * * *